US008419427B2

(12) United States Patent
Effenberger et al.

(10) Patent No.: US 8,419,427 B2
(45) Date of Patent: Apr. 16, 2013

(54) DEVICE FOR INFILTRATION OF APPROXIMAL ENAMEL LESIONS OF TEETH

(75) Inventors: Steffen Effenberger, Hamburg (DE); Hendrik Meyer-Lückel, Langwedel (DE); Sebastian Paris, Osdorf (DE); Susanne Effenberger, Hamburg (DE)

(73) Assignees: Ernst Muhlbauer GmbH & Co. KG, Norderfriedrichskoog (DE); Charite Universitatsmedizin, Berlin (DE)

( * ) Notice: Subject to any disclaimer, the term of this patent is extended or adjusted under 35 U.S.C. 154(b) by 99 days.

(21) Appl. No.: 12/808,539

(22) PCT Filed: Oct. 23, 2008

(86) PCT No.: PCT/EP2008/008968
§ 371 (c)(1),
(2), (4) Date: Aug. 12, 2010

(87) PCT Pub. No.: WO2009/077029
PCT Pub. Date: Jun. 25, 2009

(65) Prior Publication Data
US 2010/0297575 A1   Nov. 25, 2010

(30) Foreign Application Priority Data

Dec. 18, 2007   (EP) .................................. 07024508

(51) Int. Cl.
*A61C 5/14*   (2006.01)
(52) U.S. Cl.
USPC .......................................................... 433/136

(58) Field of Classification Search .............. 433/39–40, 433/80, 82, 88–90, 136, 141, 146–149, 215–217.1; 132/321–329, 309; 601/162–164
See application file for complete search history.

(56) References Cited

U.S. PATENT DOCUMENTS

| 1,624,054 | A |   | 4/1927  | Khune |         |
|-----------|---|---|---------|-------|---------|
| 3,472,247 | A | * | 10/1969 | Borsum et al. | 132/322 |
| 3,828,804 | A | * | 8/1974  | Ely   | 132/323 |
| 4,031,908 | A | * | 6/1977  | Ting  | 132/322 |
| 4,214,598 | A | * | 7/1980  | Lee   | 132/325 |
| 4,483,676 | A |   | 11/1984 | Thierman |      |
| 4,880,382 | A | * | 11/1989 | Moret et al. | 433/118 |
| 5,125,834 | A | * | 6/1992  | Swan  | 433/80  |
| 5,588,452 | A | * | 12/1996 | Peck  | 132/321 |
| 6,085,760 | A | * | 7/2000  | Chodorow | 132/323 |

(Continued)

FOREIGN PATENT DOCUMENTS

| DE | 377 764 C     | 6/1923  |
| DE | 91 06 538 U1  | 10/1991 |
| EP | 1 769 773 A   | 4/2007  |
| GB | 191 846 A     | 1/1923  |
| WO | WO2006/011003 A | 2/2006 |

*Primary Examiner* — Yogesh Patel
(74) *Attorney, Agent, or Firm* — Alix, Yale & Ristas, LLP (57) ABSTRACT

The device for infiltration of approximal tooth surfaces, with a flexible planar element and with a holder into which the planar element is clamped, is characterized in that the planar element is a liquid-impermeable plastic film which has a surface area for taking up a liquid to be used for treatment, and in that the holder is a bow-shaped element with a web and two lateral arms which extend from the latter and are arranged in an arc-shape or U-shape, to which the plastic film is connected in a liquid-impermeable manner.

18 Claims, 5 Drawing Sheets

U.S. PATENT DOCUMENTS

| | | | |
|---|---|---|---|
| 6,482,007 B2 * | 11/2002 | Stanwich et al. | 433/149 |
| 2002/0081550 A1 * | 6/2002 | Karazivan | 433/80 |
| 2005/0205107 A1 * | 9/2005 | Ochs | 132/323 |
| 2005/0271999 A1 | 12/2005 | Fishburne | |
| 2006/0000486 A1 | 1/2006 | Davis | |
| 2006/0127845 A1 | 6/2006 | Khouri | |
| 2007/0079847 A1 * | 4/2007 | Sampson | 132/323 |
| 2007/0157946 A1 * | 7/2007 | Lui et al. | 132/323 |

* cited by examiner

DEVICE FOR INFILTRATION OF APPROXIMAL ENAMEL LESIONS OF TEETH

BACKGROUND

The invention relates to a device for infiltration of approximal tooth surfaces, with a flexible planar element, and with a holder into which the planar element is clamped.

With such a device, the planar element can be used not only to clean interdental spaces, but also to provide these with fluoride compounds (US 2006/0000486). For this purpose, the cloth-shaped or cloth-like planar element is soaked with the fluoride compound. In this way, both tooth surfaces lying opposite each other in the interspace are wetted at the same time.

Wetting on both sides is in many cases undesirable. This is particularly so when a dental restoration material for incipient caries is to be applied. Caries is characterized by progressive demineralization of the enamel by metabolic products of bacteria, resulting in the first instance in small lesions called white spots. If left untreated, these lead to cavities that finally destroy the tooth. Even lesions that are detected at an early stage can rarely be remineralized. They are usually treated by traditional filling therapy in which healthy tooth substance also has to be removed. Filling therapy is particularly disadvantageous in the case of approximal caries, i.e. caries present on the aspect of the tooth facing the neighboring tooth, since healthy tooth substance increasingly has to be removed in order to gain access. However, given the poor accessibility, even for toothbrushes, approximal caries occurs much more frequently than caries on smooth surfaces (outer (vestibular) and inner (lingual/palatal) aspects of the teeth).

The need to remove healthy tooth substance is largely avoided by the method of infiltration of enamel lesions, in which method an infiltrant, a liquid with a high coefficient of penetration, is introduced into the existing lesion and is polymerized there, if necessary after the less porous surface layer of the caries has been removed using an etching agent (e.g. an acid gel) in order to open the pores of the damaged area. The lesion is thus protected against the entry of bacteria and/or the metabolic products thereof. For approximal use of the infiltrant, special application aids are needed because of the difficulty of access.

For this purpose, it is known to use films as aids for applying substances to approximal surfaces of teeth.

German laid-open specification DE 10216950 A1 describes applying a fluoride gel by means of a flexible film. To make it easier to insert the film into the interdental space, it can be strengthened along the film edge by an integrated thread. A continuation of this thread is intended to avoid the film being swallowed.

The published international application WO 00/66025 A1 describes a method for applying and hardening dental protective varnishes by means of a fabric strip. The latter contains areas with substrate materials in which the substances are made available. At its ends, the strip is typically made of dental floss or of other filaments, in order to facilitate insertion into the interdental space. The strips have sufficient mobility in order to adapt to the dental arch, and/or the substrate material is adapted to the dental arch.

Moreover, European patent application EP 1854445 A1 discloses polymer plastic films for use as application strips for infiltration of approximal enamel lesions. The application strips consist of plastic films measuring ca. 20 cm in length, onto which a coating is applied that carries an infiltrant or an etching agent.

However, all the application strips described to date have the disadvantage that their dimensions and mobility make them difficult to handle. Handling is also made difficult by the fact that polymer plastic films can statically charge and then adhere to the hands or gloves of the user. Mobility also poses the danger of the substances that are to be transferred coming into contact with healthy enamel or even with the oral mucosa. Moreover, they can only be used with two hands in the oral cavity, such that the user no longer has a hand free with which to insert another device (dental mirror, etc.). Moreover, in the case of the rear molars for example, the user has to place the fingers deep in the oral cavity in order to bring the films correctly into position in the interdental space. The limited space for working in and the field of view are thus restricted. Woven materials such as dental floss have the disadvantage that they are not resistant to the infiltrants to be used, since they are very movable, even with considerable thickness of filament.

An object is to overcome the disadvantages of known application strips.

SUMMARY

The planar element is a liquid-impermeable plastic film, which has a surface area for taking up a liquid to be used for treatment, and the holder is a bow-shaped element with a web and with two lateral arms which extend from the latter and which are arranged in an arc shape or U shape, to which the plastic film is connected in a liquid-impermeable manner.

In contrast to the prior art mentioned at the outset, the plastic film is not permeable to liquid, with the result that said liquid can be applied and act only on one side. The planar element is also not just simply inserted into two guides and lies on the holder without any sealing. By contrast, the liquid-impermeable connection to the bow-shaped element ensures that no liquid can get to the other side, even at the location where it holds the planar element.

In an advantageous embodiment, the film is transparent at least in part. This greatly improves the field of view during treatment.

The film is limited in its mobility by the bow-shaped element, such that the user can use it easily with one hand in the oral cavity.

Bow-shaped holders are known in the dental field, for example for dental floss or abrasive tapes for cleaning approximal tooth surfaces. Examples that may be mentioned here are US 2005/0271999 and EP 1449495 A2. However, these holders have to be made very stable, since they have to withstand considerable forces when cleaning the tooth surfaces or interdental spaces, and they therefore have to be suitably large. This problem does not arise in the infiltration of approximal enamel lesions, since in this case only a thin film has to be introduced into the interdental space widened slightly by a separating wedge or the like, and preferably, after removal of the separating wedge, the film is held by the adjacent teeth themselves, with no further frictional forces being exerted on the film. One would therefore expect that a person skilled in the art would not take these known bow-shaped holders into consideration when seeking a solution to the problem and that he would even regard them as disadvantageous, in view of the additional costs and of the additional space they take up. This preconception is now overcome. Moreover, for the use, the bow-shaped holders have to be resistant to aggressive media, in particular hydrochloric acid, which does not have to be the case of the bow-shaped holders of the prior art.

The film provided in the device includes a separate area that can take up or already contains a liquid. When the liquid is brought into contact with the approximal enamel lesion, this area delivers the liquid to the lesion (infiltrates it). The infiltration liquid can be a constituent of a gel.

The bow-shaped element has greater stiffness than the film, as a result of which the film is stabilized. Uncontrolled movements, twisting, kinking or bending of the application strip are thus avoided. The bow-shaped element is preferably made of a thermoplastic. It is preferably an injection-molded part. It has an upper web and two lateral arms. The web and arms are preferably formed in one piece. The web and arms are arranged in an arc shape or U shape. The span width of the arc can preferably narrow toward the ends. The bow-shaped element has a size allowing it to receive at least one film corresponding to the approximal surface of a human tooth. It has a size that makes it possible to insert the device fully into the oral cavity and use it in an interdental space. The bow-shaped element has a span width of 5 to 35 mm, preferably 10 to 25 mm, particularly preferably 15 to 20 mm. The lateral arms have a length corresponding approximately to the height of a crown of a tooth. The lateral arms are preferably slightly longer than the neighboring crowns are high. The web has a length of 3 to 25 mm, preferably 4 to 20 mm, particularly preferably 5 to 15 mm.

The bow-shaped element can have a predetermined flexural strength. Particularly in the area of the web, it has a flexural strength that makes it possible to slightly bend this device transversely with respect to the occlusal surface in order to better adapt the clamped plastic film to a curved approximal tooth surface.

For this purpose, the bow-shaped element can alternatively be designed in such a way that the film is forced from the outset into an arc shape transversely with respect to the occlusal surface. The web is then formed in an arc shape transversely with respect to the occlusal surface of the teeth. The arms extend substantially perpendicular to the bending of the web. The film substantially follows the profile of the arc and is securely connected to the arms and to the web.

A further alternative is to choose plastic films that are so extensible that they easily adapt themselves to the tooth surface.

The plastic film is securely connected to the bow-shaped element. The plastic film can be clamped in the bow-shaped element. However, non-destructive separation is preferably not provided. The plastic film is preferably welded or adhesively bonded onto the bow-shaped element.

The device is preferably designed as a disposable part and is intended to be used only once. Repeated use is, however, also possible.

The plastic film is largely transparent or transparent at least in part, preferably with the entire film being transparent. This generally permits a better field of vision and in particular permits a good view of the treatment area.

The plastic film is preferably made of a plastic that is easy to weld to the plastic of the bow-shaped element. The plastic film expediently has a high tear strength while at the same time having a low thickness. The plastic film has in particular a good chemical resistance to the liquids that are to be taken up. The plastic is preferably a polyolefin, e.g. polyethylene (HDPE, LDPE), polypropylene, polystyrene, polyvinyl chloride or polyacrylate, a polyamide, a polyester or polycarbonate. Here, plastics are also to be understood as ones based on natural polymers, e.g. celluloid. Polyethylene terephthalate (PET), e.g. Hostaphan®, is particularly preferred. It is important that the film is resistant to aggressive media, in particular hydrochloric acid. It must last substantially undamaged for the maximum period of contact of about one hour.

The plastic film, particularly in the untensioned state, has a degree of inherent stability, such that compression, for example, is avoided. Moreover, the plastic film has to have a thickness permitting insertion into the interdental space. The plastic film, together with the area for taking up the liquid or containing the liquid, preferably has a thickness allowing insertion into the interdental space. The thickness of the plastic film is less than about 1 mm, preferably less than about 0.5 mm, more preferably less than about 0.3 mm, more preferably less than about 0.1 mm, particularly preferably less than about 0.05 mm.

The height and length of the plastic film are adapted to the bow-shaped element. The dimensions ensure that contact of the liquid with the neighboring tooth is largely avoided. This protection against contamination is further improved if the film is sealingly connected to the bow-shaped element on three sides, following the bow profile.

The area for taking up the liquid, that is to say the actual application field, is configured such that it can take up a suitable amount of substance and can also easily release this substance again. It should be configured such that the substance remains substantially limited to the application field.

In the simplest case, the area for taking up the liquid is a roughened surface of the film. This can be achieved, for example, by thermal treatment of the film.

Moreover, a cover on the film can serve as the application field. This cover is composed, for example, of foam, woven fabric (synthetic or natural), paper or felt.

It is also possible to produce the cover by flocking the film. The flock and the adhesive have good chemical resistance to the liquids that are to be taken up. The flock is applied preferably as a design flock (partial application field) or alternatively as a whole-surface flock. The adhesion promoters used are preferably dispersion adhesive for screen printing, polyurethane adhesive, or contact adhesive from the company CHT or the company KIWO. The flock types used are preferably polyether sulfone or polyester, polymethylmethacrylate, polypropylene, aromatic polyamides, special aramid, viscose. The fiber lengths are less than 2 mm, preferably approximately 0.2 mm. The fiber thickness is less than 6.6 dtex, preferably approximately 0.9 dtex. The fibers can preferably be white so as to be better able to see the applied media, or they can be of any desired color.

The roughened film or the cover together with the film have a thickness of less than about 1 mm, preferably less than about 0.5 mm, more preferably less than about 0.4 mm, particularly preferably less than about 0.3 mm.

The application field can moreover be designed as a depression or multiplicity of depressions and/or as a hollow or multiplicity of hollows. The depressions are preferably formed by laser-working of a film or by the joining of two films, where one of the films has a continuous recess or a multiplicity of continuous recesses which, after the films are joined, form(s) the depression or multiplicity of depressions. The join can be produced by heat-sealing, for example. The depressions and/or hollows are preferably circular to oval. The depressions can additionally have a previously described cover. Hollows are preferably produced by deep-drawing. The thickness of the application field is less than about 1 mm, preferably less than about 0.5 mm, more preferably less than about 0.3 mm, more preferably less than about 0.1 mm, particularly preferably less than about 0.05 mm.

The plastic film with the application field can also have areas that contain cleaning elements. The cleaning areas are arranged to the right and/or left of the application field, but preferably to the right or left. The cleaning areas are formed by strippers. Located between the strippers there are depressions, preferably groove-shaped depressions, which preferably extend transversely with respect to the stripping direction. However, other geometries can also be used. They serve to strip off excess infiltration material.

The depressions are preferably formed by the joining of two films, where one of the films has a recess or a multiplicity of recesses which, after the films are joined, form(s) the depressions. The strippers are formed by the remaining film material.

The strippers can also be formed by slats that are connected otherwise to the film. The slats can, for example, be secured thermally or applied by means of an adhesive. Slats secured in this way are preferably made of elastic materials, for example silicone or rubber.

The strippers are preferably arranged obliquely, such that the substance can better flow off the tooth surface during stripping. The strippers can also be angled or arc-shaped on both sides, such that excess liquid to be taken up from the tooth surface can flow off easily.

Overflow grooves can additionally extend longitudinally to the stripping direction, and/or the depressions between the strippers are open at least toward one end of the film strip. This prevents a situation where a suction effect in the depressions arises and liquid is thereby sucked out of the infiltrated lesion again. For this reason, strongly absorbent cleaning elements, for example of woven fabrics or cotton pads, are not especially suitable for the infiltration method.

The various areas of the application strip can be differently colored or can assume different colors.

The bow-shaped element can have means for securing a handle. Inserting and positioning the application aid by means of a handle has the advantage that the user does not have to place the fingers in the oral cavity in order to maneuver the device. This permits firstly a further improved view of the treatment area and also better controlled use of the device according to the invention. The handle is preferably mounted on top of and/or to the side of the web of the bow-shaped element or on one of the arms. It can be secured via a hinge-like connection, such that the handle can be folded to the side or bent after insertion of the device. The connection could alternatively involve a predetermined break, such that the handle can be broken off after the device has been introduced.

Directly before use, the liquid can be applied to the application field of the plastic film with conventional dental brushes or syringes.

It is possible, but disadvantageous, for the infiltration liquid to be applied to the application area already at the time of manufacture. The products usually have shelf lives of several years and must therefore be able to be stored safely. For an infiltration liquid or an etching gel to be stored ready for use on the application field over a relatively long period of time, very high demands also have to be placed, for example, on the chemical resistance of the film. Moreover, the liquid may contain volatile components, which would require a gas-tight and/or vapor-tight packaging of the whole application aid. In addition, the infiltration liquids have pronounced creep characteristics and could spread out from the application area and across the whole device during the storage time. This would render the device unusable. The infiltration liquid contains polymerization initiators which, for example, have to be stored in a manner protected from light. The liquid is therefore advantageously stored separately from the application strip or plastic film.

In order to store the liquid in a stable and safe manner over a period of several months to years, it is preferable to use light-protected, chemically resistant, gas-tight and/or vapor-tight syringes. The syringes are preferably made of glass and/or plastic, particularly preferred plastics being cycloolefin polymers (COP) and/or cycloolefin copolymers (COG). The syringe can be designed as a carpule, a simple pressure syringe or a rotary syringe.

In one embodiment, the liquid is not applied to the application field of the film until the application strip is already placed in the interdental space. This therefore further improves the protection against other areas being contaminated with the liquid. The safety of use is increased. More targeted dosing is also possible.

For this purpose, provision can be made for the liquid to be conveyed to the application field of the film by way of the bow-shaped element. For this purpose, the bow-shaped element contains one or more channels. These channels are preferably contained in the web of the bow-shaped element. The channels lead from an opening in the bow-shaped element to the film, particularly preferably directly to the application field, and specifically from the direction of the web and/or the arms. A syringe can, for example, be attached to the opening or can be inserted with a tight fit into the opening, and the liquid can be conveyed through the channels to the film. Suitable syringes and application devices for these are described in European patent specification EP 0714638 B1, for example.

The syringe can also be integrated in the above-described handle. This can be done in such a way that the syringe can be actuated from outside the oral cavity.

If, as has been described above, the application strip is designed as a composite film, it is also possible for the application strip to have channels between the two films. These channels then represent continuations of the channels in the bow-shaped element and lead from the latter to the application field of the plastic film and preferably extend into the application field, such that a pocket perforated on one side is obtained for the liquid.

The channels of the bow-shaped element and the channels of the application strip can be strengthened, supplemented or connected by additional elements, for example a tube element.

Provision can also be made for a dose of the liquid to be stored directly in or on the bow-shaped element. In one embodiment of the invention, a film pouch is used for this purpose, which film pouch empties into the above-described channels when pressure is applied. Preferred film pouch arrangements are described in the published international application WO 2007/017225 A2, for example. The use of capsules or cavities with discharging pistons is also possible.

As was mentioned above, the film can contain areas for removing excess liquid. Alternatively, a separate device can be provided which has a bow-shaped element and a plastic film with the described cleaning elements, but no area for application (infiltration). This device expediently forms, with said device for infiltration, an overall device in the form of a treatment set, which additionally has one or more separating wedges of different size for widening the interdental space, an etching agent, a drying agent and/or an application aid for the etching agent, and the infiltration liquid. If the device for infiltration also has strippers, the device that contains only strippers can also be omitted from the set.

Separating wedges that are suitable in principle for the set are described, for example, in U.S. Pat. No. 6,482,007 B2. The drying agent for the lesion is preferably a highly volatile, toxicologically safe solvent, in particular one containing ethanol. The set can also contain brushes and/or syringes for directly applying the various materials to the application aids or also to the tooth.

The separating wedges preferably have a triangular cross section, it having proven particularly advantageous if one of the three points of the triangular cross section is flattened, such that the cross section is trapezoid, since this facilitates the introduction of the film if the flattened point is directed away from the gum.

The device for infiltration can of course be used just as well for treatment with a liquid or gel-like etching agent.

BRIEF DESCRIPTION OF THE DRAWINGS

The invention is described below on the basis of advantageous illustrative embodiments and with reference to the attached drawings, in which.

DETAILED DESCRIPTION

Figure 1:
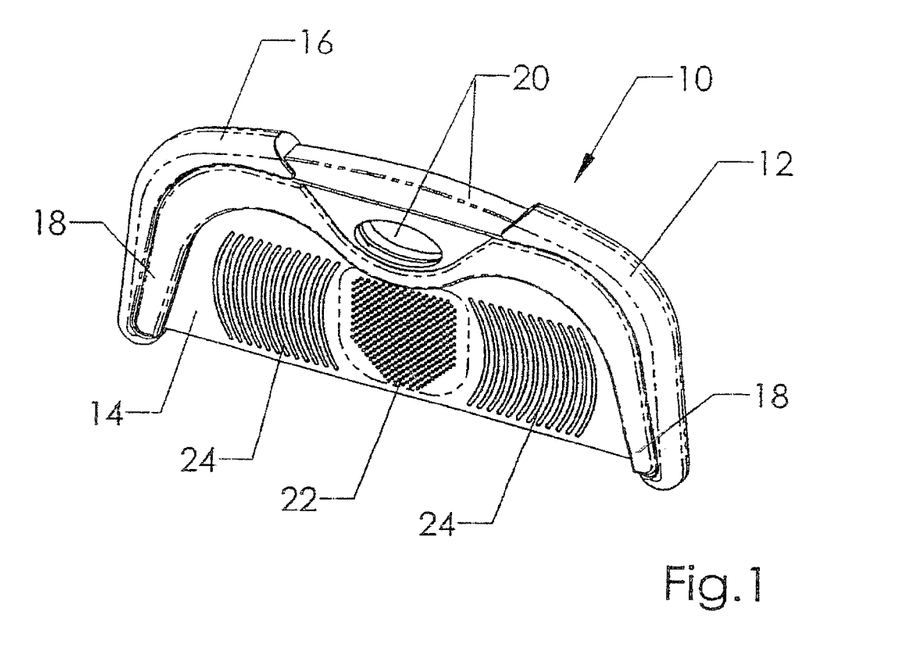
FIG. 1 shows a perspective view of a device.
Figure 2:
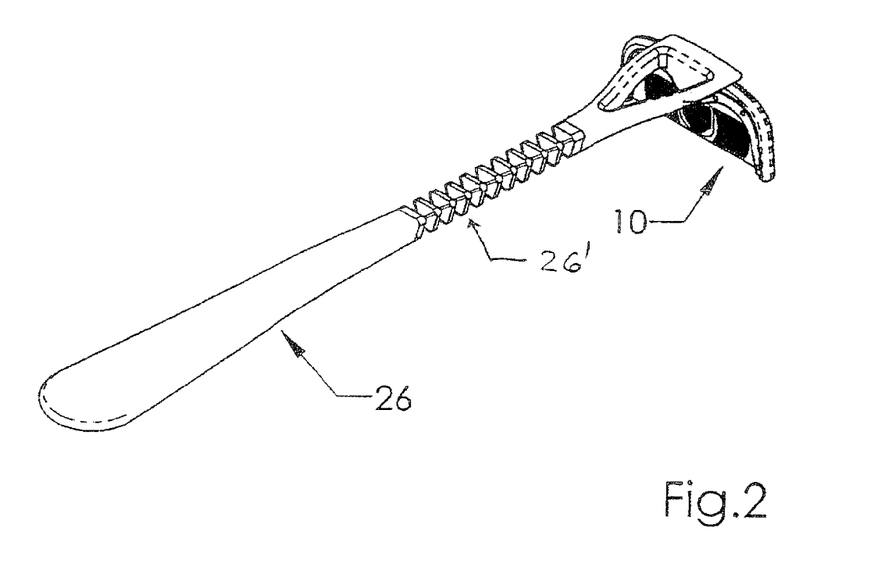
FIG. 2 shows the embodiment from FIG. 1, with a handle mounted thereon.

FIG. 1 shows an embodiment of the device 10, having a bow-shaped element 12 which is substantially U-shaped and which has a web 16 and two arms 18. The bow-shaped element 12 is advantageously made of plastic, in particular an injection-molded part. A plastic film 14 is secured between the web 16 and the arms 18, the lower edge of the plastic film 14 reaching as far as the free ends of the arms 18. The plastic film has depressions on one side in the area 22, onto or into which depressions an infiltration agent can be applied or introduced. Slats 24, which are used to strip off excess liquid, are provided to the right and left alongside the area 22 of the depressions. The web 16 is provided with recesses 20, which are used to secure a handle 26 shown in FIG. 2. The handle 26 can have a bendable area 26'. This handle can also be mounted laterally on an arm 18 and advantageously secured with a hinge-like connecting area on the arm 18, such that the handle 26 can be folded after the device 10 has been placed in the interdental space. The securing can also be achieved in the form of a predetermined break, such that the handle 26 can be removed from the oral cavity after the device 10 has been put in place.

Figure 3:
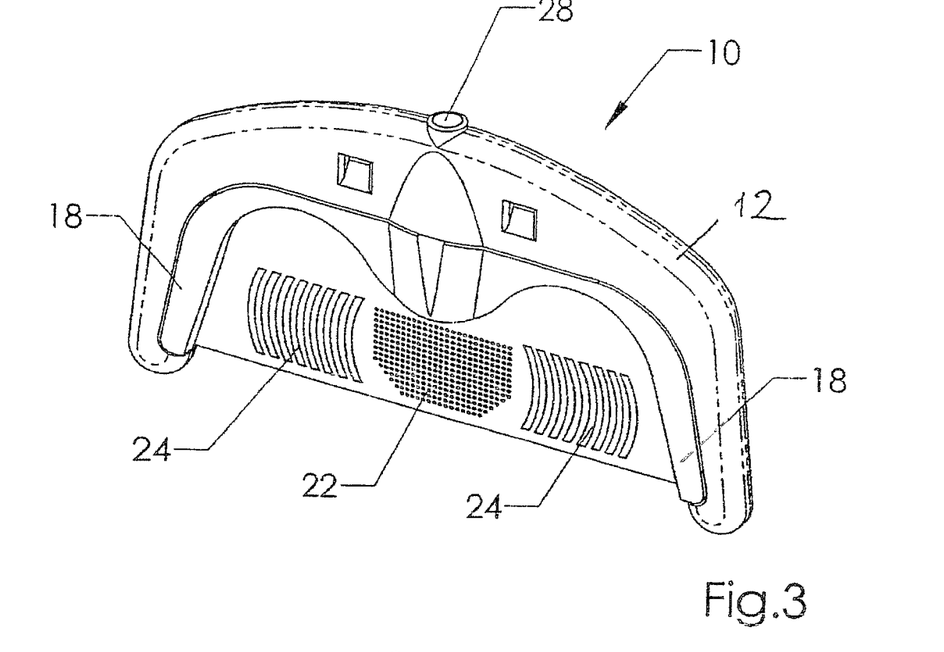
FIG. 3 shows an embodiment with channels for supplying the liquid for the infiltration.
Figure 4:
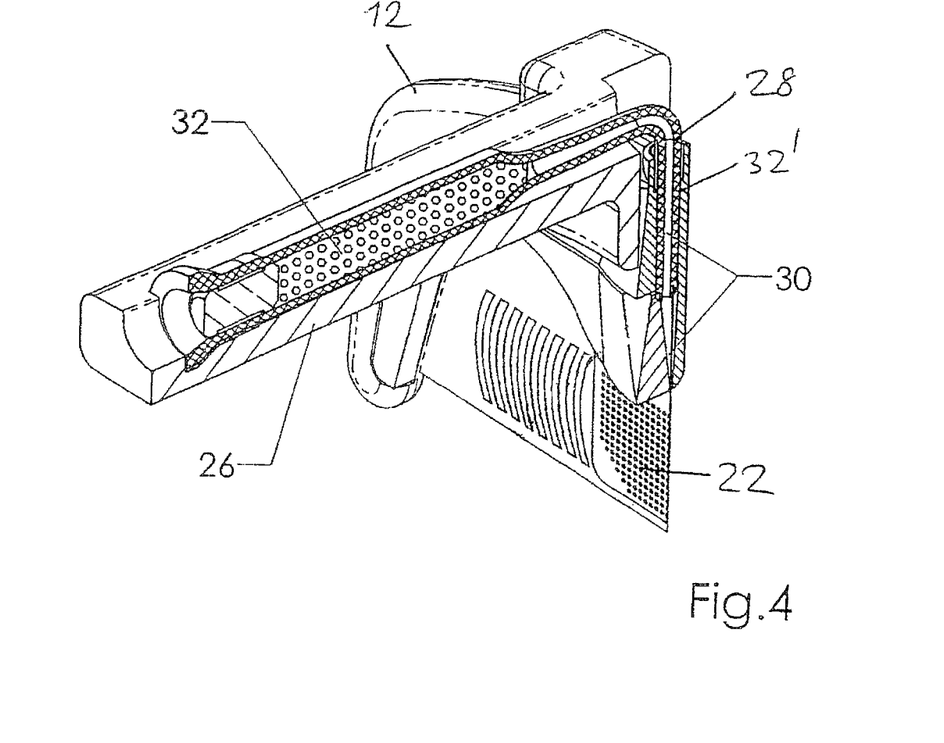
FIG. 4 shows, in partial cross section, an embodiment with channels, and with a syringe arranged in a handle and used for supplying the liquid for the infiltration.

The embodiments in FIGS. 3 and 4 differ from the embodiment in FIG. 1 by having channels 30 (shown in FIG. 4) which lead from an upper opening 28 to the area 22 where the depressions for the infiltration agent are provided. In the embodiment in FIG. 3, the infiltration agent, in particular a liquid, could be poured in at the top and would then move to the area 22 by gravity. In the embodiment in FIG. 4, this purpose is served by a syringe 32, which is arranged in the handle 26 and is attached via the angled front area 32' to the opening 28 or to the bow-shaped element 12. Although the opening 28 and the front area 32' of the syringe are slightly conical here, they can have different shapes adapted to each other in such a way that they permit a close-fitting attachment.

Figure 5:
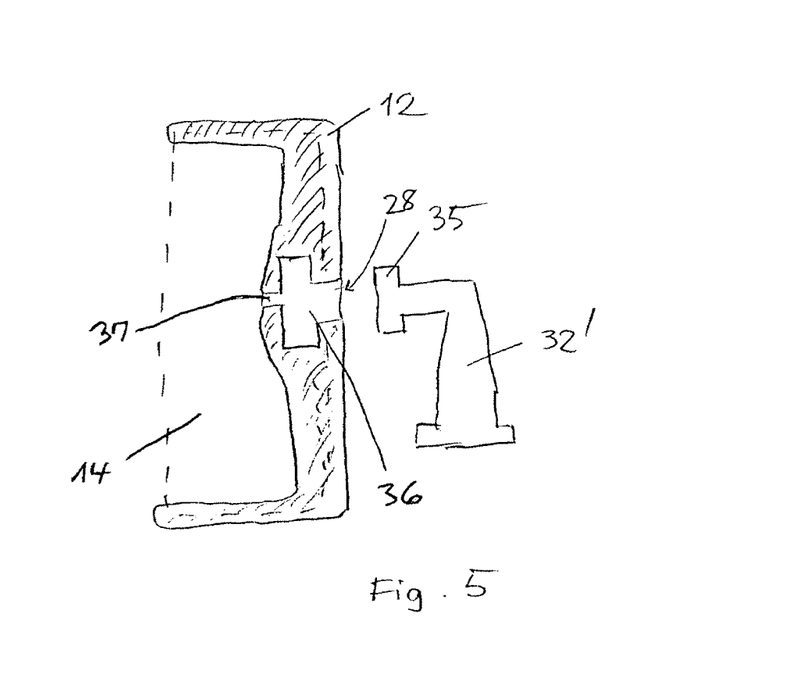
FIG. 5 shows an exploded view of part of the device.

FIG. 5 shows a preferred configuration of the front area 32', which comprises a disk-shaped element 35 that matches a corresponding opening 28. The contour and the internal dimensions of the opening 28 substantially correspond to the external dimensions of the front area 32' with the disk-shaped element 35. FIG. 5 shows only one half of the bow-shaped element 12, provided in the area of the opening 28 with a depression 36, which is likewise provided in the other half of the bow-shaped element 12 symmetrical with respect to this half. The disk-shaped element 28 fits into these depressions 36. After the disk-shaped element 28 has been inserted into the depression 36 of one half of the element 12, the film 14, shown by broken lines in FIG. 5, and the second half of the bow-shaped element 12 are laid on top and connected to each other by adhesive bonding, welding or the like. The film 14 in this case preferably has two layers, with one layer being arranged under and one layer over the disk-shaped element 35, such that the liquid can then pass between the film layers and then out through corresponding perforations of the film 14 on one side. The channel 30 can also be connected by a tube element 37 to the channels of the application strip 14.

Figure 6:
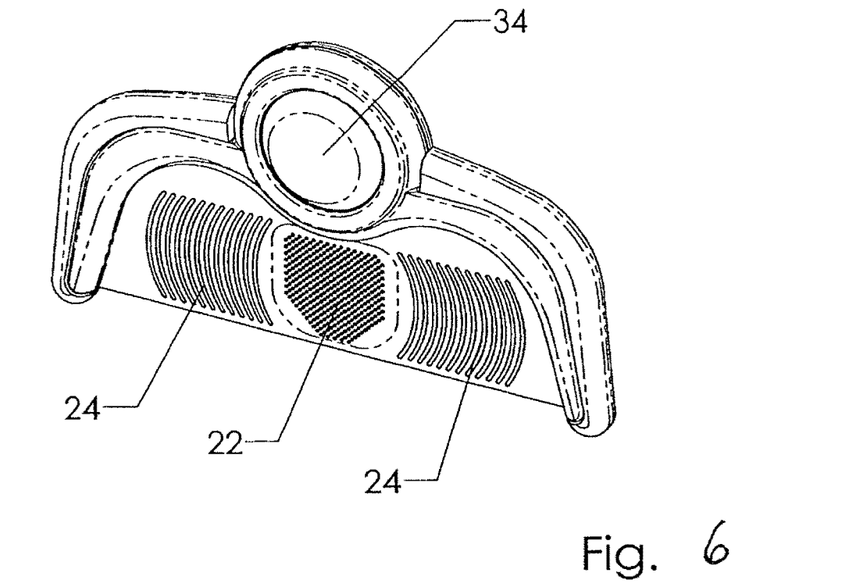
FIG. 6 shows an embodiment with a film pouch for the liquid.
Figure 7:
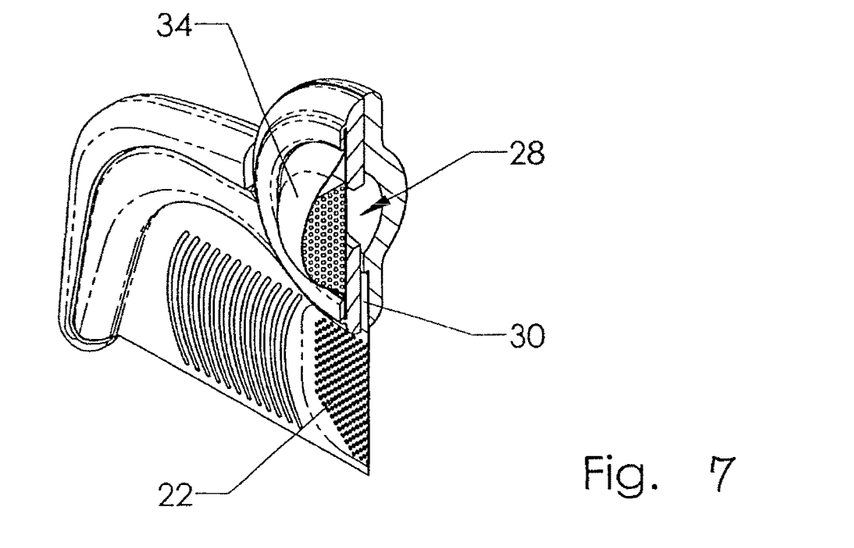
FIG. 7 shows a cross-sectional view of the embodiment from FIG. 6.

In the embodiment in FIGS. 6 and 7, a film pouch 34, which contains the infiltration liquid, is mounted in the area of the opening 28. When pressure is exerted on the film pouch 34, this infiltration agent can then be moved into the area 22 with the depressions for the infiltration agent. The film pouch 34 in this case preferably has, in the lower area, a predetermined break (not shown in the figure) which bursts when pressure is exerted, such that the liquid can pass into the area 22.

Figure 8:
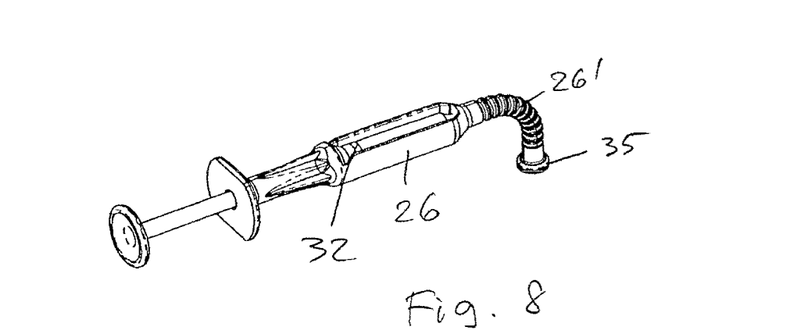
FIG. 8 shows another embodiment of the device.

FIG. 8 shows a part of the application aid 10 with handle 26 and with syringe 32 arranged therein, and with an area 26' that is bent or bendable like a hinge. The area 26' is tubular. The area 26' is preferably bellows-like. However, it can also be composed of smooth tubes of ductile material (metal, plastic), in particular of a lengthways bonding of different materials. The figure also shows the disk-shaped element 35, which can be connected to the opening 28 of the bow-shaped element 12.

The angled front area 32' of the syringe can, as is also shown in FIG. 5, be designed as a separate element that can be connected to the syringe 32 in a detachable manner. A suitable (Luer) cone can then be provided on the syringe, which preferably has a union nut 38 (shown in FIG. 9) for securing the connection (Luer lock).

Figure 9:
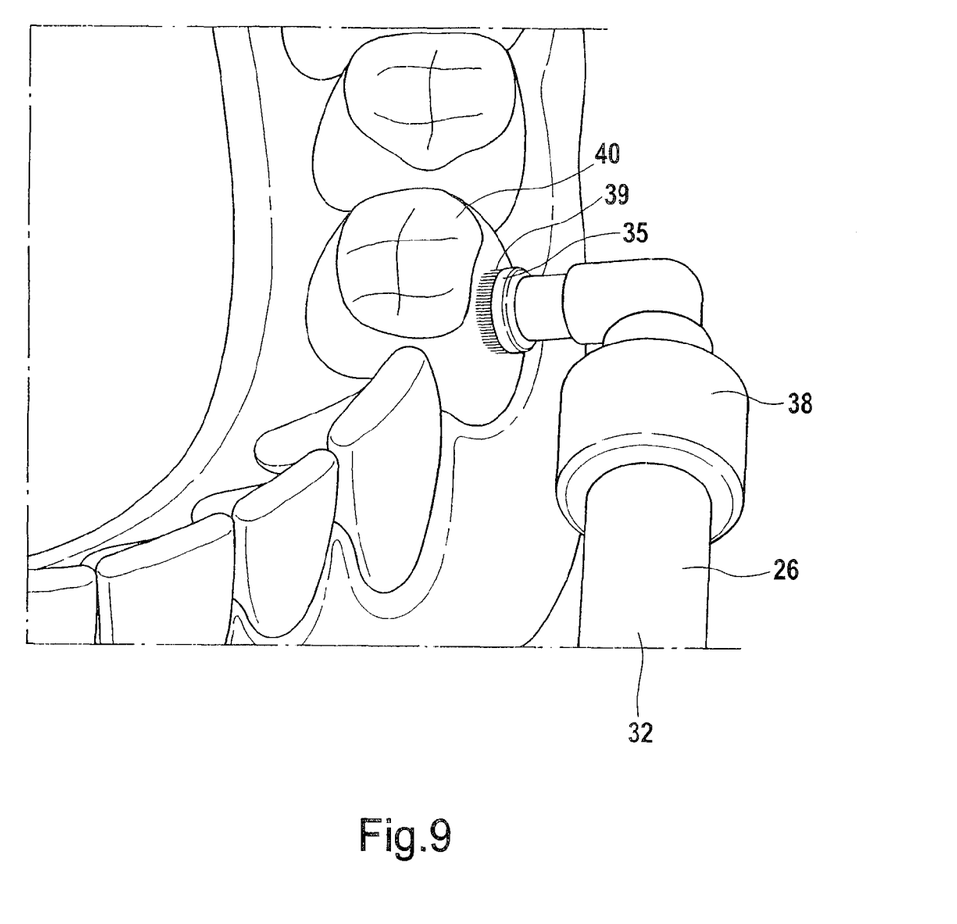
FIG. 9 shows another use of part of the device.

FIG. 9 also shows another use of part of the device, which part can be a component of a set or kit. A flock 39 is provided on the disk-shaped end 35 of a handle 26 or of a syringe 32, which flock 39 is wetted by the liquid and can be used to treat the exposed surfaces of teeth 40. The angled shape is not absolutely necessary.

The invention claimed is:

1. A device for infiltration of approximal tooth surfaces, with a flexible planar element and with a holder into which the planar element is secured, characterized in that the planar element is a liquid-impermeable composite plastic film having two planar surfaces defined by two films, one of the planar surfaces having a surface area for taking up a liquid to be used for treatment, and in that the holder is a bow-shaped element with a web and with two lateral arms which extend from the web and which are arranged in an arc shape or U shape, to which the plastic film is connected in a liquid-impermeable manner, and said bow-shaped element has one or more channels, which lead from an opening in the bow-shaped element to the surface area of the film, where the liquid is to be taken up, wherein the planar element has one or more channels corresponding in number with the one or more bow-shaped element channels, the one or more planar element channels disposed between the two films and comprising continuations of the one or more bow-shaped element channels, the one or more planar element channels leading from the bow-shaped element to the surface area for taking up the liquid to be used for treatment.

2. The device as claimed in claim 1, characterized in that the opening is arranged on a top face of the web.

3. The device as claimed in claim 2, characterized in that the composite film is connected to the bow-shaped element in a liquid-impermeable manner on three sides.

4. The device as claimed in claim 2, characterized in that the composite film is connected to the bow-shaped element by welding or adhesive bonding.

5. The device as claimed in claim 1, characterized in that the composite film is connected to the bow-shaped element in a liquid-impermeable manner on three sides.

6. The device as claimed in claim 1, characterized in that the composite film is connected to the bow-shaped element by welding or adhesive bonding.

7. The device as claimed in claim 1, characterized in that the composite film is clamped in the bow-shaped element.

8. The device as claimed in claim 1, characterized in that the composite film is transparent at least in part.

9. The device as claimed in claim 1, characterized in that the composite film, in the area for taking up the liquid, is provided with depressions or hollows.

10. The device as claimed in claim 9, characterized in that the depressions or hollows are formed by the joining of the two films, of which one is provided with recesses.

11. The device as claimed in claim 1, characterized in that the composite film extends as far as the free ends of the arms.

12. The device as claimed in claim 1, characterized in that the bow-shaped element is made of plastic.

13. The device as claimed in claim 10, characterized in that the bow-shaped element is made of thermoplastic.

14. The device as claimed in claim 1, characterized in that the bow-shaped element is an injection-molded part.

15. The device as claimed in claim 1, characterized in that the device has a handle.

16. The device as claimed in claim 15, characterized in that the handle has a hinge-like or bendable area between a main part and an end on which the bow-shaped element is secured.

17. The device as claimed in claim 15, characterized in that the handle is provided with a syringe for the liquid.

18. The device as claimed in claim 1, characterized in that the device additionally has, in the form of a set or kit, one or more separating wedges of different size for widening the interdental space, an etching agent, a drying agent and/or an application aid for the etching agent, and the infiltration liquid.

* * * * *